United States Patent [19]

Lovell

[11] 4,213,988

[45] *Jul. 22, 1980

[54] INSECTICIDAL 1,5-BIS(α,α,α-TRIFLUORO-P-TOLYL)-1,4-PENTADIEN-3-ONE (1,4,5,6-TETRAHYDRO-2-PYRIMIDINYL)-HYDRAZONES

[75] Inventor: James B. Lovell, Pennington, N.J.

[73] Assignee: American Cyanamid Company, Stamford, Conn.

[*] Notice: The portion of the term of this patent subsequent to May 2, 1995, has been disclaimed.

[21] Appl. No.: 4,645

[22] Filed: Jan. 19, 1979

Related U.S. Application Data

[60] Division of Ser. No. 883,775, Mar. 6, 1978, Pat. No. 4,163,102, which is a continuation-in-part of Ser. No. 793,116, May 2, 1977, abandoned.

[51] Int. Cl.$^2$ .............................................. A01N 9/22
[52] U.S. Cl. ..................................................... 424/251
[58] Field of Search ........................................ 424/251

[56] References Cited

U.S. PATENT DOCUMENTS 3,878,201  4/1975  Tomcufcik .......................... 424/273

*Primary Examiner*—V. D. Turner
*Attorney, Agent, or Firm*—H. G. Jackson

[57] ABSTRACT

The invention is 1,5-bis(α,α,α-trifluoro-p-tolyl)-1,4-pentadien-3-one (1,4,5,6-tetrahydro-2-pyrimidinyl)hydrazones which are useful insecticides.

5 Claims, No Drawings

INSECTICIDAL 1,5-BIS(α,α,α-TRIFLUORO-P-TOLYL)-1,4-PENTADIEN-3-ONE (1,4,5,6-TETRAHYDRO-2-PYRIMIDINYL)HYDRAZONES

This is a division of application Ser. No. 883,775 filed Mar. 6, 1978 which is now U.S. Pat. No. 4,163,102 filed July 31, 1979 which was a continuation-in-part application Ser. No. 793,116 filed May 2, 1977 now abandoned.

The invention is compounds of the formula:

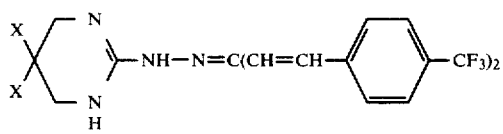

wherein X is hydrogen or methyl which are useful as insecticides, especially for the control of fire ants and cockroaches.

Pentadien-3-one substituted amido hydrazones are described in U.S. Pat. No. 3,878,201 (1975) as antimalarial and anti-tubercular agents for warm-blooded animals.

EXAMPLE 1

Preparation of 1,5-bis(α,α,α-Trifluoro-p-tolyl)-1,4-pentadien-3-one (1,4,5,6-tetrahydro-5,5-dimethyl-2-pyrimidinyl)hydrazone.

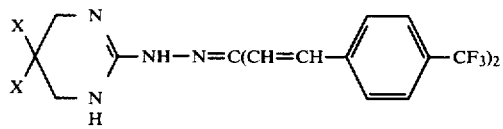

To a mixture of 2.1 g of 5,5-dimethyl-1,4,5,6-tetrahydropyridinium-2-ylhydrazine hydroiodide and 3.2 g of 1,5-bis(α,α,α-trifluoro-p-tolyl)-1,4-pentadien-3-one in 6 ml of absolute ethanol was added one drop of 47% hydriodic acid. The mixture was heated at reflux for 2 to 3 hours and then cooled in ice. The yellow hydroiodide salt which precipitated was collected by filtration and washed with ethanol.

The hydroiodide salt was neutralized by stirring with 15 ml of ethyl acetate and 15 ml of saturated sodium carbonate solution. The ethyl acetate mixture was separated from the aqueous phase, dried over magnesium sulfate, and concentrated to give a red oil. The oil was mixed with a little ether, and the mixture refrigerated. The resulting solids were collected and washed with ether and amounted to 1.2 g, melting point 163.5°–164.5° C.

Analysis calculated for $C_{25}H_{24}F_6N_4$: C, 60.72; H, 4.89; N, 11.33. Found: C, 60.54; H, 4.73; N, 10.43.

The product exists in different crystalline forms, and when recrystallized from isopropyl alcohol, has a melting point of 189°–191° C.

EXAMPLE 2

Preparation of 1,5-bis(α,α,α-trifluoro-p-tolyl)-1,4-Pentadien-3-one (1,4,5,6-tetrahydro-2-pyrimidinyl)hydrazone

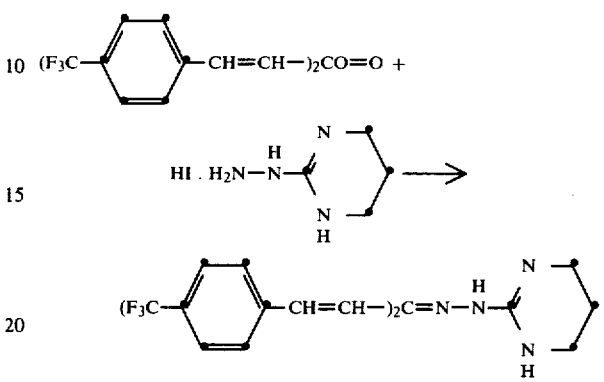

27.7 Grams (0.075 mol) of the dienone and 18.0 grams (0.075 mol) of the hydrazine were reacted together in refluxing isopropanol for 3 to 4 hours. The isopropanol was stripped away leaving a pale yellow solid which was washed thoroughly with ether. The yellow solid was stirred with 200 ml of ether and 50 ml of saturated sodium carbonate. After 15 minutes, the ether layer was dried and concentrated leaving a bright yellow solid weighing 25.0 grams (72% theory). A small sample was recrystallized from φCH₃/hexane giving a bright yellow solid with melting point 196°–197° C.

Analyses calculated for $N_4F_6C_{23}H_{20}$: C, 59.24; H, 4.29; N, 12.02. Found: C, 58.55; H, 4.53; N, 12.00.

EXAMPLE 3

The insecticidal activity of the compounds of the invention are further demonstrated by the following tests, wherein pentadienone hydrazones are evaluated as stomach poisons against test insect species at rates of from 500 to 10,000 ppm. Insect species utilized in these evaluations are: American cockroaches [*Periplaneta americana* (Linnaeus)] and German cockroaches [*Blattella germanica* (Linnaeus)]. Test formulations and evaluation procedures are as follows:

A. 100 Milligrams of 100% pure compound were placed in 20 g of creamy peanut butter and thoroughly mixed. This is equivalent to a concentration of approximately 0.5% or 5000 ppm.

B. 5.0 Grams of peanut butter served as the control. Approximately 5.0 g of bait were placed in a 3 cm × 1 cm high plastic cup. The plastic cup of bait and a water wick were placed in a cage 8 inches in diameter and 2.5 inches high. The bottom of the cage was an 8-inch diameter plate of glass resting on a ½-inch rim which extended inward from the stainless steel side. Twenty (20) adult male German cockroaches or 12 nymphs of American cockroaches were placed in each cage. The cage was covered with a 16-mesh copper wire screen lid. The cages were held at approximately 27° C.

The results are in the following table:

TABLE I

| Compound | Concentration in ppm | Percent Mortality | | | |
|---|---|---|---|---|---|
| | | German Cockroaches Days Post-treatment | | American Cockroaches Days Post-treatment | |
| | | 7 | 14 | 7 | 14 |
| (CF₃—⟨phenyl⟩—CH=CH—)₂C=N—NH—⟨N(CH₃)₂/N ring⟩ | 5000 | 100 | 100 | 17* | 92 |
| Check (Control) | — | 0 | 0 | 8 | 8 |

*Several affected.

EXAMPLE 4

Red Imported Fire Ants [*Solenopsis invicta* (Buren)]

TABLE II

Evaluation of Test Compound for the Control of the Imported Fire Ant
(Three Ant Colonies, Each Concentration)

| Structure | Percent Concentration | Bait Acceptance | 6-Week Results Number of Colonies Alive or Dead | Remarks |
|---|---|---|---|---|
| (CF₃—⟨phenyl⟩—CH=CH—)₂C=N—NH—⟨N(CH₃)₂/N ring⟩ | 0.05 | Fair to Excellent | All 3 dead | |
| | 1.0 | | Killed 1 of 2 | Only majors Alive in 2 Mounds at 3 weeks. |
| | 0.1 | Attracted the Ants | Killed 3 to 6 at 7 weeks | 1 Killed and 5 sick mounds at 3 weeks |

Red imported fire ants [*Solenopsis invicta* (Buren)] obtained out-of-doors under natural conditions were used in the imported fire ant screen. Approximately 0.5 cu. ft. of an active ant mound was placed in a plastic tub (13"×13"×8") and aged in the laboratory for 3 days before use. The top 3 inches on the inside of the tub were dusted with talc to prevent the ants from escaping. Water was added to the mounds as needed both before and after treatment to help keep them from becoming too dry. The compounds were dispersed in soybean oil starting at a low concentration of approximately 0.05%. The concentration was increased at various increments to approximately 1.0%. Low concentrations were used first to determine if the compound was palatable to the ants. Approximately 7.5 g of soybean oil containing the toxicant were poured over a small wad of absorbent cotton in a 3-oz. Dixie cup. The side of the Dixie cup was placed on top of the mound. Usually 3 tubs were used per concentration. Mortality counts and/or ratings were made at 6 weeks after treatment or longer if warranted. The temperature of the holding rooms was approximately 26° C. with a relative humidity of approximately 50%.

Data obtained are reported in the Table below.

EXAMPLE 5

German Cockroach Bait Toxicant Test—[*Blatella Germanica* (Linnaeus)]

Test Procedure

Tests were conducted in cages 20.32 cm in diameter and 6.35 cm in height. The circular side was made of stainless steel which supported a piece of glass 20.32 cm in diameter for the bottom. The cages were capped with 16-mesh copper wire screen lids. One hundred, 25. and 6.25 mg of technical compound were added to five grams of creamy peanut butter in a plastic cup (inside dimensions of 8 mm high and 30 mm in diameter) to yield final concentrations of 2.0, 0.5, and 0.125%, respectively. The mixtures were each stirred for two minutes. One cup of treated bait plus one cup of untreated lab chow (five grams) to serve as a choice of food, a 100 ml water wick, and 20 adult, male German cockroaches were placed in each cage. The cages were held at approximately 27° C. and 35% R. H. for mortality counts. Data obtained are reported in the table below.

TABLE III
EVALUATION OF PENTADIENONE HYDRAZONES AS INSECTICIDES
PERCENT MORTALITY

| Structure | German Cockroaches 11-Day Mortality | | |
|---|---|---|---|
| | 2.0% | 0.5% | 0.125% |
| $(F_3C-\text{C}_6H_4)-CH=CH-)_2 C=N-NH-$(pyrrolidinyl with NH) | 100 | 100 | 100 |
| $(F_3C-\text{C}_6H_4)-CH=CH-)_2 C=N-NH-$(dimethyl-substituted ring with NH) | 100 | 100 | 100 |

EXAMPLE 6

Imported Fire Ant Bait Toxicant Tests (*Solenopsis invicta* Buren)

Test Procedure

Tests were conducted in 30 ml disposable plastic medicine cups (40 mm ID at the top, tapering to 32 mm ID at the bottom, 38 mm high). A hole (6 mm diam.) was drilled through the bottom of each cup and a layer of plaster of Paris and builders' cement (9:1 ratio) was poured over the bottom. The plastic mixture covers the hole and acts as a wick to draw up water when the cup is placed on a saturated ¼" foam pad. The cups were placed in a tray and covered by another tray inverted to prevent rapid evaporation of water from the foam pad. Moisture is necessary to keep the humidity in the the cups high and thereby prevent dessiccation of the ants. The cement is added to make a hard mixture through which the ants cannot tunnel and escape.

Twenty worker ants from field-collected colonies were placed in each test chamber about 24 hours preceding start of the test. This pretreatment holding period allows time for recovery of the ants from handling and for orientation to the containers.

Candidate chemicals were dissolved directly in the food material; e.g., soybean oil. The toxic solution was offered to the ants on cotton swabs saturated with the material and placed in the test chamber in small vial caps. Preliminary tests were conducted at concentrations of 1.0, 0.1, and 0.01 percent.

The ants were allowed to feed as desired on the toxic bait for 24 hours. After this exposure period, the toxicant was removed from the chamber and the ants remained without food for an additional 24 hours. At the end of this time new vial caps containing cotton swabs saturated with soybean oil were placed in the chamber and left for the remainder of the test period. Knockdown and mortality counts were made at intervals of 1, 2, 3, 6, 8, 10 and 14 days following initial exposure. Each test consisted of 3 replications. Room temperature was maintained at 75±2 F. Data are reported in the table below.

TABLE IV
EVALUATION OF PENTADIENONE HYDRAZONES AS INSECTICIDES
PERCENT MORTALITY

| Structure | Red Imported Fire Ant 14-Day Mortality | |
|---|---|---|
| | 1.0% | 0.1% |
| $(F_3C-\text{C}_6H_4)-CH=CH-)_2 C=N-NH-$(pyrrolidinyl with NH) | 69 | 100 |
| $(F_3C-\text{C}_6H_4)-CH=CH-)_2 C=N-NH-$(dimethyl-substituted ring with NH) | 100 | 95 |

EXAMPLE 7

The insecticidal activity of the compounds of this invention is demonstrated by the following tests, wherein pentadienone hydrazones are evaluated against test insect species at rates of from 10 to 1000 ppm. Test formulations and procedures used for evaluation are as follows:

Test Formulations.

A. 100 Milligrams of the test material is weighed, placed in a funnel over a 113 g narrow-mouth bottle, and rinsed into the bottle with a 35 ml scoop of acetone, followed by a scoop of water and another scoop of acetone to yield 1000 ppm in 65% acetone. If the material is not soluble, it is broken up with a glass rod and used as a suspension.

B. This stock solution ("A") is used to make 300 ppm solutions or suspensions by pipetting 30 ml of "A" into a bottle containing 70 ml of 50% acetone to yield 300 ppm. Further dilutions in 50% acetone are made as required.

C. Tests requiring 10 ppm acetone solutions: 1 ml of "A" is pipetted into 99 ml of acetone to yield 10 ppm. Additional dilutions are made using 50% acetone as required.

Initial Tests

Tobacco Budworm—[*Heliothis virescens* (Fabricus)].

A cotton plant with two true leaves expanded is dipped for 3 seconds with agitation in 300 ppm solution. A 1.27 cm to 1.91 cm square of cheesecloth with about 50 to 100 budworm eggs 0–24 hours old is also dipped in the test solution and placed on a leaf of the cotton plant, all being placed in the hood to dry. The leaf with the treated budworm eggs is removed from the plant and placed in a 226 g Dixie cup with a wet 5 cm piece of dental wick and covered with a lid. The other leaf is placed in a similar cup with a wick and a piece of cheesecloth infested with 50–100 newly hatched larvae is added before covering the cup with a lid. After 3 days at 80° F., 50% r.h., observations of egg hatch are made, as well as kill of newly hatched larvae, any inhibition of feeding, or interference of any sort with normal development.

Secondary Tests

Tobacco Budworm—[*Heliothis virenscens* (Fabricus)]—Third Instar

Three cotton plants with just expanded cotyledons are dipped in 1000 ppm solution and placed in the hood to dry. When dry, each cotyledon is cut in half, and 10 are each placed in a 28 g plastic medicine cup containing a 1.25 cm dental wick saturated with water and one third-instar budworm larva is added. The cup is capped and held for 3 days at 80° F., 50% r.h., after which mortality counts are made. Compounds killing more than 75% of the larvae are further tested.

Cabbage Looper—[*Trichoplusia ni* (Hübner)]—Third Instar

A true leaf of a cotton plan is dipped into the test solution, agitated for 3 seconds, and removed to dry in an exhaust hood. When dry, the leaf is placed in a 9.0 cm petri dish with moist filter paper on the bottom. Ten third instar larvae are added and the lid placed on the dish. Mortality counts are made after 3 days at 80° F. and 50±10% r.h. Compounds killing more than 75% of the loopers are further tested.

Southern Armyworm—*Spodoptera eridania* (Cramer)

Sieva lima bean plants pruned back to two expanded 3 to 4 inches primary leaves are dipped 3 seconds with agitation in the treatment solutions and then set in a hood to dry. After the leaves are dry they are excised, and each excised leaf is placed in a 4-inch petri dish containing a piece of moist filter paper and ten third-instar Southern armyworm larvae approximately ⅜ of an inch long. The petri dishes are covered and placed in a holding room for 2 days at a temperature of 80° F. and 50% relative humidity. Mortality counts are made after 2 days.

Seven days after the plants are treated, leaves are again excised and the test procedure repeated. Mortality of armyworms occurring in this test demonstrates the residual activity of the compounds on the treated leaves.

Data obtained are reported in the Table below.

TABLE V

| | Evaluation of Test Compound for Controlling Insects on Cotton Plants | | | | | | | | | | | | | |
|---|---|---|---|---|---|---|---|---|---|---|---|---|---|---|
| | Budworm | | | | | | Third Instar Tobacco Budworm | | Cabbage Looper | | Southern Armyworm | | | |
| | Eggs | | | Larvae | | | | | | | | | | |
| Compound | 300 ppm | 100 ppm | 10 ppm | 300 ppm | 100 ppm | 10 ppm | 1000 ppm | 100 ppm | 1000 ppm | 100 ppm | 1000 ppm | 100 ppm | 10 ppm | 7 Days |
| 1,5-bis(α,α,α-Trifluoro-p-tolyl)-1,4-pentadien-3-one (1,4,5,6-tetrahydro-5,5-dimethyl-2-pyrimidinyl)-hydrazone | 0 | — | — | 100 | 100 | 0 | 100 | 90 100 | 100 | 100 | 100 | 100 | 40 | 100 |
| 1,5-bis(α,α,α-Trifluoro-p-tolyl)-1,4-pentadien-3-one (1,4,5,6-tetrahydro-2-pyrimidinyl)hydrazone | 0 | — | — | 100 | 100 | 0 | 100 | 100 | 100 | 100 | 100 | 100 | 70 | 100 |

I claim:

1. A method for controlling fire ants and cockroaches comprising contacting the insects, their habitat, breeding grounds or feed with an insecticidally effective amount of a compound of the formula:

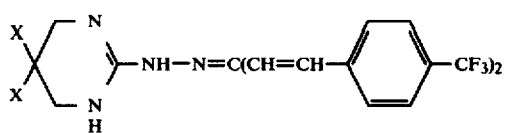

wherein X is hydrogen or methyl.

2. A method according to claim 1 wherein the compound is 1,5-bis(α,α,α-trifluoro-p-tolyl)-1,4-pentadien-3-one (1,4,5,6-tetrahydro-5,5-dimethyl-2-pyrimidinyl)-hydrazone.

3. A method according to claim 1 wherein the compound is 1,5-bis(α,α,α-trifluoro-p-tolyl)1,4,-pentadien-3-one (1,4,5,6-tetrahydro-2-pyrimidinyl)hydrazone.

4. A method according to claim 1 wherein the insects are fire ants.

5. A method according to claim 1 wherein the insects are cockroaches.

* * * * *